United States Patent
Bolomey et al.

(10) Patent No.: US 7,129,371 B2
(45) Date of Patent: Oct. 31, 2006

(54) BENZENE PHOSPHINIC ACID WITH IMPROVED FLOWABILITY

(75) Inventors: Pascal V. Bolomey, Solon, OH (US); Thomas W. Dickerson, Greenwell Springs, LA (US); James D. Love, Hudson, OH (US); William C. Wang, Baton Rouge, LA (US)

(73) Assignee: Ferro Corporation, Cleveland, OH (US)

( * ) Notice: Subject to any disclaimer, the term of this patent is extended or adjusted under 35 U.S.C. 154(b) by 670 days.

(21) Appl. No.: 10/606,945

(22) Filed: Jun. 26, 2003

(65) Prior Publication Data

US 2005/0070732 A1    Mar. 31, 2005

Related U.S. Application Data

(60) Provisional application No. 60/393,162, filed on Jul. 2, 2002.

(51) Int. Cl.
    *C07F 9/02*    (2006.01)
(52) U.S. Cl. ........................................ 558/71
(58) Field of Classification Search .................. 558/71
    See application file for complete search history.

(56) References Cited

U.S. PATENT DOCUMENTS 4,849,134 A    7/1989    Georlette et al.
4,965,021 A    10/1990   Georlette et al.

FOREIGN PATENT DOCUMENTS

EP           377995 A2 *    7/1990

* cited by examiner

*Primary Examiner*—Thurman K. Page
*Assistant Examiner*—Lalitha Nagubandi
(74) *Attorney, Agent, or Firm*—Rankin, Hill, Porter & Clark LLP

(57) ABSTRACT

The present invention provides BZPA products with improved flowability and two methods of producing such BZPA products. Both methods successfully produce BZPA products that are not prone to agglomerate upon storage, and thus the flowability of such BZPA products does not degrade over time. The first method includes mechanically forming the BZPA crystals into large compacted pellets or briquettes without the introduction of any additives or binders. The compacted pellets are large enough that the physical and chemical effects that occur on the surface of small crystal particles are eliminated or minimized, but small enough that the BZPA can be easily handled and used in commercial applications. The second method includes adding a substantially inert anti-caking agent to the BZPA crystals to minimize or retard their tendency to agglomerate. The preferred anti-caking agent is silicon dioxide ($SiO_2$), which is blended with the BZPA crystals in small amounts.

9 Claims, 1 Drawing Sheet

BENZENE PHOSPHINIC ACID WITH IMPROVED FLOWABILITY

RELATED APPLICATIONS

This application claims the benefit and priority of provisional application Ser. No. 60/393,162 filed Jul. 2, 2002 entitled Benzene Phosphinic Acid With Improved Flowability.

BACKGROUND OF THE INVENTION

1. Field of Invention

The present invention relates to a method of producing benzene phosphinic acid having improved flowability.

2. Description of Related Art

Benzene phosphinic acid (hereinafter sometimes referred to as "BZPA") is sold in bulk quantities for use in a variety of applications including, for example, as a color stabilizer where hindered phenols are not effective, a modifying agent for use in polyamides, an antioxidant, an intermediate for forming metallic salts used as stabilizers, an accelerator for organic peroxide catalysts, a free radical promoter in emulsion polymerization, an improver of polysiloxane resins, and a corrosion inhibitor on thin aluminum surfaces. BZPA is typically prepared by the hydrolysis of benzene phosphonous dichloride. The resulting aqueous slurry is treated by centrifugation or other filtration means to separate the BZPA particles, which are typically small needle-shape crystals, from the aqueous medium. Upon drying, solid crystals of BZPA are obtained in a powder-like form.

Due to its hygroscopicity and other physical and chemical characteristics, BZPA crystals have a strong tendency to agglomerate. Depending upon various conditions such as the length of time the BZPA crystals are stored, the storage conditions, the storage container shape and size, the temperature and the humidity, the extent of agglomeration may vary from a few lumps or clumps within the powder to a complete solid mass throughout the container. Agglomeration, which is also sometimes described as caking or compaction, renders BZPA difficult to handle, because the material does not flow freely out of the container into which it has been packaged. The agglomeration problem can present a potential safety risk (i.e., back strain) to the individuals who attempt to remove the BZPA from shipping and storage containers.

BRIEF SUMMARY OF THE INVENTION

The present invention provides BZPA products with improved flowability and multiple methods of producing such BZPA products. The methods of the present invention successfully produce BZPA products that are not prone to agglomerate upon storage, and thus the flowability of such BZPA products does not degrade over time.

The first method comprises mechanically forming the BZPA crystals into large compacted pellets or briquettes without the introduction of any additives or binders. The compacted pellets are large enough that the physical and chemical effects that occur on the surface of small crystal particles are eliminated or minimized, but small enough that the BZPA can be easily handled and used in commercial applications.

The second method comprises adding a substantially inert an anti-caking agent to the BZPA crystals to minimize or retard their tendency to agglomerate. The preferred anti-caking agent is silicon dioxide ($SiO_2$), which is blended with the BZPA crystals in small amounts.

The foregoing and other features of the invention are hereinafter more fully described in the following description, which also sets forth in detail certain illustrative embodiments of the invention, these being indicative, however, of but a few of the various ways in which the principles of the present invention may be employed.

DETAILED DESCRIPTION OF THE INVENTION

Figure 1:
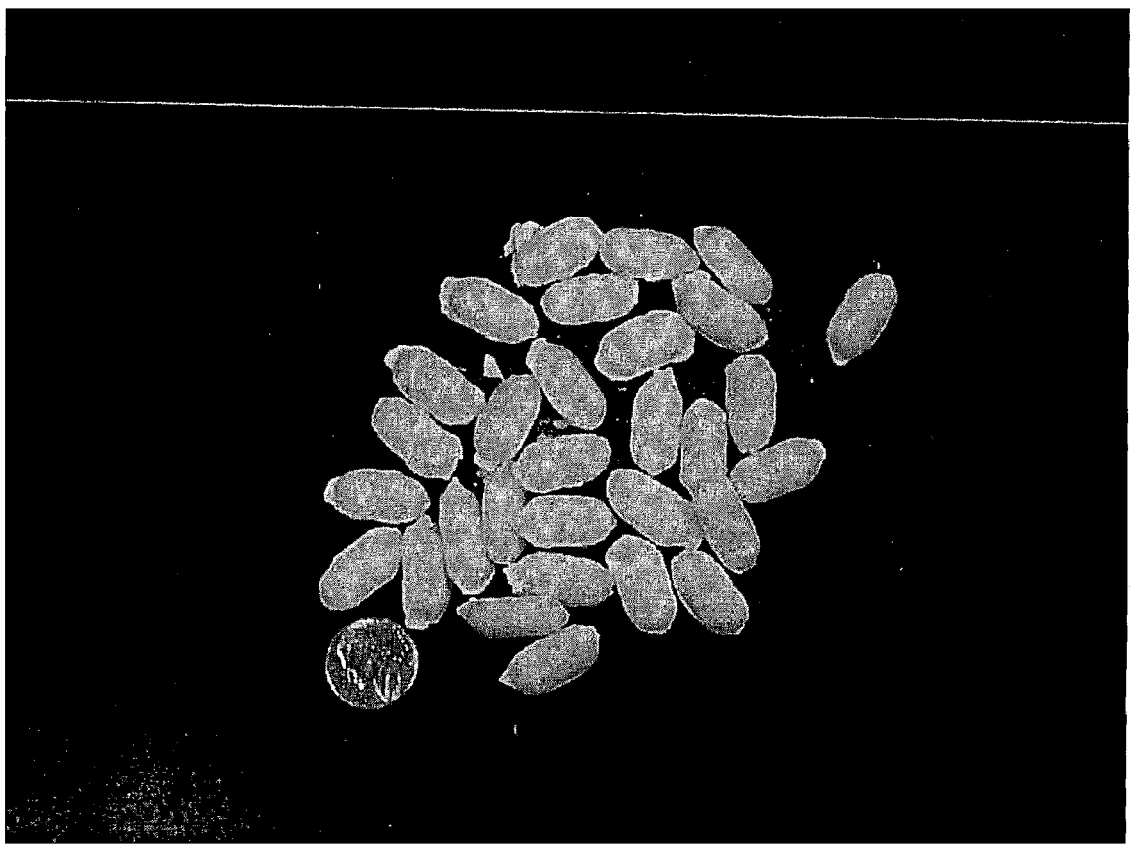
FIG. 1 is a photograph of BZPA in pellet form according to the first method of the invention.

As noted above, the present invention provides two methods of producing BZPA products having improved flowability. Each method is separately discussed below.

Cold Compacted Benzene Phosphinic Acid

The first method of forming BZPA products with improved flowability comprises mechanically forming the BZPA crystals into compacted pellets, tablets or briquettes, preferably without the introduction of any additives or binders. The compacted pellets are large enough that the physical and chemical effects that occur on the surface of small crystal particles are eliminated or minimized, but small enough that the BZPA can be easily handled and used in commercial applications. Compacted pellets having any dimension can be produced in accordance with the invention, but pellets having an average diameter of about 1 mm to about 25 mm are preferred, with pellets of about 20 mm being most preferred.

Conventional cold-compaction equipment can be used to form the pellets. Suitable equipment is available, for example, from K. R. KOMAREK, Inc. of Elk Grove Village, Ill. The equipment uses a feed screw and rollers to press the BZPA crystals into the desired pellets or briquettes. The amount of pressure applied during the formation of the pellets or briquettes should be the minimum pressure sufficient to agglomerate the particles. Excessive pressure can make the pellets or briquettes difficult to further process (e.g., crush or dissolve). A pressure on the rollers of about 7,000 N/cm, or roughly about 10,000 psi, is sufficient. Compaction is accomplished without the need for added heat, and can be done at ambient temperatures.

The pellets or briquettes, once formed, are durable enough to withstand ordinary handling and processing without creating substantial quantities of dust. The pellets remain flowable and can be moved by pellet handling equipment and even hand tools such as shovels.

Flowable Benzene Phosphinic Acid Powder

The second method comprises adding a substantially inert anti-caking agent to the BZPA crystals to minimize or retard their tendency to agglomerate. By inert the inventors mean an agent that does not adversely effect the desired properties of the BZPA. The preferred anti-caking agent is silicon dioxide ($SiO_2$), which is blended with the BZPA crystals in small amounts. The amount of silicon dioxide is preferably the least amount that is necessary to prevent agglomeration. Amounts of less than 5000 ppm have been determined to be suitable, with amounts of about 1,000 to 2,000 ppm being preferred.

The size of the silicon dioxide used in the invention is not per se critical, but powders, typically having a mean average particle size between 25–35 microns, are presently most preferred. The silicon dioxide powders are believed to interfere with both the chemical and physical processes that cause agglomeration.

Both methods successfully produce BZPA products that are not prone to agglomerate upon storage, and thus the flowability of such BZPA products does not degrade over time. The pellet form can be crushed, if necessary, prior to use if BZPA in powder form is desired. Crushing can be accomplished by conventional means, which are well known in the art. Typically, however, the pellets or briquettes are simply contacted with a solvent and allowed to dissolve. A typical preferred solvent is water at an elevated temperature.

It will be appreciated that the methods of the present invention are not necessarily limited to BZPA in its pure acid form, but can also be extended to BZPA derivatives and related compounds. Examples include salts of BZPA such as sodium benzene phosphinate and potassium benzene phosphinate. These salts are typically sold as aqueous solutions, but can be obtained as dry solids by evaporating the water. Other suitable phosphorous derivatives include toluene phosphinic acid and salts of toluene phosphinate.

At present, BZPA is commercially available only in a crystalline powder form from a variety of suppliers. As noted above, this form of BZPA presents handling and storage problems due to agglomeration. Pressing the BZPA crystals into pellets or briquettes in accordance with the first method of the invention prevents caking or agglomeration of the BZPA crystals during storage and shipment, and facilitates their use in later processing applications. Blending the BZPA crystals with a substantially inert anti-caking agent such as silicon dioxide in accordance with the second method of the invention also tends to retard agglomeration and results in the long-term retention of a flowable BZPA product.

The following examples are intended only to illustrate the invention.

EXAMPLE 1

Approximately 20 lbs of commercial grade BZPA crystals (available from Ferro Corporation of Cleveland, Ohio) were fed without a binder material to briquette-forming equipment (available from K. R. KOMAREK, Inc. of Elk Grove Village, Ill.) at a rate of 100 lb/hour and at ambient temperature. The briquette-forming equipment consisted of a hopper and a single feed screw made from 316 stainless steel, and two pressure rollers made from Hastelloy C. The briquette-forming equipment was used to press the BZPA crystals together to form pellets or briquettes without the addition of any binders or additives.

The formed briquettes had a semi-cylindrical shape with rounded ends. The briquette dimensions were approximately 0.8" in length and 0.4" in diameter. A photograph of the briquettes is shown in FIG. 1. A United States nickel is show in the photograph for size comparison.

The BZPA briquettes did not agglomerate upon storage. After four weeks of typical storage, the briquettes flowed readily out of a 50 lb. fiber drum container. The briquettes were determined to be mechanically strong via a drop test in which the briquettes were dropped from a height of six (6) feet onto a hard surface. The briquettes could be crushed easily to obtain discrete BZPA crystals when needed for use.

EXAMPLE 2

Eight 8-ounce glass bottles (inside diameter 2.25 inches, inside height 4.75 inches) were labeled as Samples Bottles 1A, 1B, 2A, 2B, 3A, 3B, 4A and 4B, respectively. Sample Bottles 1A and 1B were filled with 100 grams of BZPA crystals (available from Ferro Corporation of Cleveland, Ohio). Sample Bottles 2A and 2B were filled with 100 grams of BZPA crystals that had been blended with 1,000 ppm of 25–30 micron mean particle size silicon dioxide (available from PPG Industries, Inc. of Pittsburgh, Pa. as FLO-GARD SP). Sample Bottles 3A and 3B were filled with BZPA crystals that had been blended with 2,000 ppm of silicon dioxide. And, Sample Bottles 4A and 4B were filled with BZPA crystals that had been blended with 5,000 ppm of silicon dioxide.

Sample Bottles 1A, 2A, 3A and 4A were stored on a shelf at a temperature ranging from 20–25° C. for seven days. Sample Bottles 1B, 2B, 3B and 4B were stored on a shelf at a temperature ranging from 30–35° C. for seven days. After seven days, each sample bottle was tilted slowly to observe the flowability of the material inside. Regardless of the storage temperature, both BZPA control samples (i.e., Sample Bottles 1A and 1B) were solid lumps with no observable flowability whatsoever. Tilting each bottle upside down did not allow the material to flow. On the other hand, all other samples that had been spiked with silicon dioxide (i.e., Sample Bottles 2A, 2B, 3A, 3B, 4A and 4B) flowed easily when the bottles were tilted in excess of 45 degrees.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept.

What is claimed is:

1. A flowable composition of matter comprising, crystalline benzene phosphinic acid blended with silicon dioxide.

2. A flowable composition as set forth in claim 1 wherein said silicon dioxide is an inert binder.

3. A flowable, composition of matter as set forth in claim 1 wherein said benzene phosphinic acid comprises cold-compacted benzene phosphinic acid.

4. A method of forming a flowable composition comprising cold compacting crystals of benzene phosphinic acid into pellets or briquettes.

5. The method according to claim 4 wherein the pellets are free of any binders.

6. The method according to claim 4 wherein the pellets have an average particles size of from about 1 mm to about 25 mm.

7. The method according to claim 4 wherein the pellets consist essentially of benzene phosphinic acid.

8. A method of forming a flowable composition comprising blending crystals of benzene phosphinic acid with silicon dioxide.

9. The method according to claim 7 wherein the amount of silicon dioxide is less than about 5,000 ppm.

* * * * *